United States Patent [19]
Toda et al.

[11] Patent Number: 5,266,588
[45] Date of Patent: Nov. 30, 1993

[54] COMPOUND PRODUCED BY A STRAIN OF MICROTETRASPORA HAVING ANTIBACTERIAL AND NEURITOGENIC ACTIVITY

[75] Inventors: Soichiro Toda, Ohmiya; Takashi Tsuno, Tokyo; Satoshi Yamamoto, Yokohama; Toshifumi Hasegawa, Tokyo; Osamu Tenmyo, Yokohama, all of Japan; Mary P. Rosser, Mariden, Conn.

[73] Assignee: Bristol-Myers Squibb Company, New York, N.Y.

[21] Appl. No.: 951,976

[22] Filed: Sep. 25, 1992

[51] Int. Cl.⁵ .................. A61K 31/40; C07D 405/12
[52] U.S. Cl. .................................. 514/423; 548/517
[58] Field of Search ..................... 548/517; 514/423

[56] References Cited

U.S. PATENT DOCUMENTS

| | | | |
|---|---|---|---|
| 5,075,305 | 12/1991 | Hobbs et al. | 514/235.8 |
| 5,082,670 | 1/1992 | Gage et al. | 424/570 |
| 5,098,902 | 3/1992 | Hobbs et al. | 514/231.5 |

FOREIGN PATENT DOCUMENTS 2-172955  7/1990  Japan ................. 514/235.8

OTHER PUBLICATIONS

E. B. Shirling and D. Gottlieb, "Methods for Characterization of Streptomyces Species" Intern. J. Syst. Bact. 16, (1966) 313-340.

S. A. Waksman, In "The Actinomycetes. vol. II. Classification, Identification and Description of Genera and Species" The Williams & Wilkins Co., Baltimore, 1961, 318-334.

T. Arai, In "Culture Media for Acetinomycete" The Society for Acetinomycetes Japan, 1975.

Gauze, et al. "Problems in the Classification of Antagonistic Actinomycetes" State Publishing House for Medical Literature, Medzig, Moscow, 1957.

Lechevalier, et al. "A Critical Evaluation of the General of Aerobic Actinomycetes" In The Actinomycetales (H. Prauser, ed.) pp. 393–405, Jena, Gustav Fisher Verlag, 1970.

J. L. Staneck & G. D. Roberts, "Simplified Approach to Identification of Aerobic Actinomycetes by Thin-Layer Chromatography" *Applied Microbiology,* 28, 1974, 226–231.

Lechevalier, et al., "Chemotaxonomy of Aerobic Actinomycetes: Phospholipid Composition,", Biochem. Syst. Ecol. 5, 1977, pp. 249–260.

Minnikin, et al., "Differentiation of *Mycobacterium, Nocardia* and Related Taxa by Thin-Layer Chromatographic Analysis of Whole-Organism Methanolysates," J. Gen Microbiol. 88, 1975 pp. 200–204.

Collins, et al., "A note on the Separation of Natural Mixtures of Bacterial Menaquinones Using Reverse--phase Thin-layer Chromatography" J. Appl. Bacteriol. 48, 1980, pp. 277–282.

Suzuki, et al., "Taxonomic Significance of Cellular Fatty Acid Composition in Some Coryneform Bacteria" Int. J. Systm. Bacteriol. 33 (1983) 188–200.

Kroppenstedt, et al. "Taxonomic Erevision of the Actinomycete Genera *Actinomadurae* and *Microtetraspora*" *System Appl. Microbiol.* 13 (1990) 148–160.

Hayakawa, et al. "Lydicamycin, A New Antibiotic of a Novel Skeletal Type. II. Physico-chemical Properties and Structure Elucidation" *J. Antibiotics* 44 (1991) 288–292.

H. Thoenen and Y. A. Barde, "Physiology of Nerve Growth Factor" *Physiol. Rev.* 60 (1980) 1284–1335.

Whittemore, et al. "The Expression Localization and Functional Significance of beta-Nerve Growth Factor in the Central Nervous System" *Brain Res. Rev.* 12 (1987) 439–464.

(List continued on next page.)

*Primary Examiner*—Mary C. Lee
*Assistant Examiner*—Joseph K. McKane
*Attorney, Agent, or Firm*—Thomas R. Savitsky

[57] ABSTRACT

Disclosed is a novel compound, designated BU-4514N, which is produced by cultivation of a novel strain of Microtetraspora, designated species T689-92. The novel compound possesses antibacterial and neuritogenic properties.

15 Claims, 3 Drawing Sheets

OTHER PUBLICATIONS

Goelet, et al., "The Long and the Short of Long-term Memory—A Molecular Framework" *Nature*, 322 (1986) 419–422.

Schwartz, et al., "Molecular Mechanisms for Memory: Second-Messenger Induced Modifications of Protein Kinases in Nerve Cells" *Ann. Rev. Neurosci.*, 10 (1987) 459–476.

Eppler, et al., "Structural Studies on a Family of cAMP-binding Proteins in the Nervous System of *Aplysia*" *J. Cell Biol.*, 102 (1986) 320–321.

Scholz, et al., "Long-Term Sensitization in *Aplysia*: Biophysical Correlates in Tail Sensory Neurons" *Science*, 235 (1987) 685–687.

Weiss, et al., "Modulation of Buccal Muscle Contractility by Serotonergic Metacerebral Cells in *Aplysia*" *J. Neurophysiol.* 42 (1979) 791–803.

Fischer, et al., "Amelioration of Cholinergic Neuron Atrophy and Spatial Memory Impairment in Aged Rats by Nerve Growth Factor" *Nature*, 329, (1987) 65–68.

Furukawa, et al., "Catecholamines Induced an Increase in Nerve Growth Factor Content in the Medium of Mouse L-M Cells" *J. Biol. Chem.*, 261 (1986) 6039–6047.

Furukawa, et al., "Regulation of Nerve Growth Factor Synthesis/Secretion by Catecholamine in Cultured Mouse Astroglial Cells" *Biochem. Biophys. Res. Commun.*, 147, (1987) 1048–1054.

Tsuji, et al., "GQ1B, A Bioactive Bioactive Ganglioside that Exhibits Novel Nerve Growth Factor (NGF)-Like Activities in the Two Neuroblastoma Cell Lines" *J. Biochem.* 94 (1983) 303–306.

Cuello, et al. "Gangliosides Potentiate in vivo and in vitro Effects of Nerve Growth Factor on Central Cholinergic Neurons" *Proc. Natl. Acad. Sci.*, 86 (1989) 2056–2060.

Wu, et al., "Stimulation of Neurite Outgrowth in Neuroblastoma Cells by Neuraminidase: Putative Role of GM1 Ganglioside in Differentiation" *J. Neurochem.* 56 (1991) 95–104.

Tsuji, et al., "Synthetic sialyl Compounds as well as Natural Gangliosides Induce Neuritogenesis in a Mouse Neuroblastoma Cell Line (Neuroza)" *J. Neurochem.* 50 (1988) 414–423.

Himi, et al. "Effect of Ginzeng Saponins on the Survival of Cerebral Cortex Neurons in Cell Cultures" *Chem. Pharm. Bull.* 37 (1989) 481–484.

Wion, et al, "1,25-Dihydroxyvitamin $D_3$ Is a Potent Inducer of Nerve Growth Factor Synthesis" *J. Neurosci. Res.*, 28 (1991) 110–114.

Huffaker, et al., "Adenosine Inhibits Cell Division and Promotes Neurite Extension in PC12 Cells" *J. Cell Physiol.*, 120 (1984) 188–196.

Guroff, et al., "The Action of Adenosine Analogs on PC12 Cells" *J. Neurochem.*, 37 (1981) 1431–1439.

Morioka, et al., "Staurosporine-induced Differentiation in a Human Neuroblastoma Cell Line, NB-1" *Agric. Biol. Chem.*, 49 (1985) 1959–1963.

Omura, et al. "Lactacystin, A Novel Microbial Metabolite, Induces Neuritogenesis of Neuroblastoma Cells" *J. Antibiotics* 44 (1991) 113–116.

Wion, et al. "Serum and Thyroid Hormones T3 and T4 Regulate Nerve Growth Factor MRNA Levels in Mouse L Cells" *FEBS Lett.*, 189 (1985) 37–41.

Wion, et al., "Retinoic Acid Increases the Expression of NGF Gene in Mouse L Cells" *Biochem. Biophys. Res. Commun.* 149 (1987) 510–514.

Wion, et al., "Phorbol 12-Myristate 13-Acetate (PMA) Increases the Expression of the Nerve Growth Factor (NGF) Gene in Mouse L-929 Fibroblasts" *FEBS Lett.*, 262 (1990) 42–44.

K. N. Prasad and S. Kumar "Role of Cyclic AMP in Differentiation of Human Neuroblastoma Cells in Culture" *Cancer*, 36 (1975) 1338–1343.

Greene et al. "Establishment of a Noradrenergic Clonal Line of Rat Adrenal Pheochromocytoma Cells Which Respond to Nerve Growth Factor" *Proc. Natl. Acad. Sci.* USA 73 (1976) 2424–2428.

Hama, et al., "Protein Kinase C as a Component of a Nerve Growth Factor-Sensitive phosphorylation System in PC12 Cells" *Proc. Natl. Acad. Sci.* USA, 83 (1986) 2353–2357.

Olson, et al. "Intraputaminal Infusion of Nerve Growth Factor to Support Adrenal Medullary Autografts in Parkinson's Disease" *Arch. Nuerol.* 48 (Apr. 1991) 373–381.

Tischler and Greene, *Nature*, 258 (1975) 341–342.

α-Acyltetramic acid moiety of BU-4514N

COMPOUND PRODUCED BY A STRAIN OF MICROTETRASPORA HAVING ANTIBACTERIAL AND NEURITOGENIC ACTIVITY

FIELD OF THE INVENTION

The present invention concerns a novel compound having neuritogenic and antibacterial activities which is produced by a novel strain of Microtetraspora.

BACKGROUND OF THE INVENTION

Substances active against microorganisms have many beneficial uses. These uses are in fields such as human health care, veterinary science, and animal husbandry. Antimicrobial agents can have many desirable effects such as preventing or curing disease and promoting the growth of animals.

New antimicrobial agents are needed for several reasons; these include intolerance of the subject to be treated to known antimicrobials, and the development of strains resistant to known antimicrobials. Therefore, characterization of any previously known microorganisms which produce new antimicrobial agents is highly desirable.

Nerve growth factor (NGF) is a protein known to be essential for the development and maintenance of certain sympathetic and sensory neurons in the peripheral nervous system (Thoenen, et al. Physiol. Rev. 60:1284-1335, 1980). Recent evidence also suggests important functions of NGF in the cholinergic neurons of the basal forebrain in the central nervous system (Whittemore, et al. Brain Res. Rev. 12:439-464, 1987). It has further been reported that in aged rodents, impairments in learning and memory are related with age-dependent decline in the forebrain of cholinergic functions (Goelet, et al. Nature 322:419-422, 1986), and that the cholinergic neurons in the nucleus basalis magnocellularis, septal-diagonal band area and striatum undergo age-dependent atrophy (Schwartz et al. Ann. Rev. neurosci 10:459-476, 1987) Thus, as in Alzheimer-type dementia in man, degenerative changes of the forebrain cholinergic system may cause age-related cognitive impairments in rodents. It is known that the central cholinergic neurons in the septal-diagonal band area, nucleus basalis and striatum are sensitive to NGF (Eppler, et al. J. Cell Biol. 102:320-321, 1986). In fact, intraventricular injections or infusions of NGF in young adult rats have been shown to prevent retrograde neuronal cell death (Scholz, et al. Science 235:685-687, 1987) and promote behavioral recovery after damage to the septohippocampal connections (Weiss, et al. J. Neurophysiol. 42:791-803, 1979). NGF also has been reported to ameliorate cholinergic neuron atrophy and spatial memory impairment in aged rats (Fischer, et al Nature 329:65-68, 1987). PC12 pheochromocytoma cells, which are regarded as an important model system for study of adrenergic neuronal differentiation (Greene, et al. Proc. Natl. Acad. Sci. USA 73:2424-2428, 1976), respond to NGF, and differentiate into sympathetic neuron-like cells, exhibiting marked hypertrophy of the cell leading to extension of slender neurites which are piloted by well defined growth cones. Although several recent studies have indicated that protein kinase C is an important component of the NGF-sensitive phosphorylation system in PC 12 cells (Hama, et al. Proc. Natl. Acad. Sci. USA 83:2353-2357, 1986), NGF-associated biochemical pathways and their relationships to neurite outgrowth have not fully been elucidated. In search for potential factors which are able to modulate NGF synthesis or to mimic NGF (stimulate cell differentiation), several compounds have been reported which are summarized in the following table.

| NGF Mimic Compounds Reported | | |
|---|---|---|
| Compound | Note | Reference |
| Catecholamines | NGF inducer | Y. Furukawa, et al. J. Biol. Chem. 261 6039-6047, 1986 |
| | | S. Furukawa, et al. Biochem. Biophys. Res. Commun. 147 1048-1054, 1987 |
| Aminoalkylester derivs. | NGF inducer | S. Furukawa, et al. Japan Open-Laid Patent: 2-172955 |
| Gangliosides | NGF-like | S. Tsuji, et al. J. Biochem. 94 303-306, 1983 |
| | | Cuello, et al. Proc. Natl. Acad. Sci. 86 2056-2060, 1989 |
| | | Wu, et al., J. Neurochem. 56 95-104, 1991 |
| | | Tsuji, et al. J. Neurochem. 50 414-423, 1988 |
| Sialyl compounds | NGF-like | Tsuji, et al. J. Neurochem. 50 414-423, 1988 |
| Saponins | Neuronotrophic activity | Himi, et al. Chem. Pharm. Bull. 37 481-484, 1989 |
| 1,25-Dihydroxy-vitamin $D_3$ | NGF inducer | Wion, et al. J. Neurosci. Res. 28 110-114, 1991 |
| Adenosine | Neuritogenesis inducer | Huffaker, et al. J. Cell Physiol. 120 188-196 1984 |
| | | Guroff, et al. J. Neurochem. 37 1431-1439, 1981 |
| Staurosporine | Differentiation inducer | Morioka, et al. Agric. Biol. Chem. 49 1959-1963, 1985 |
| Lactacystin | Neuritogenesis inducer | Omura, et al. J. Antibiotics 44 113-116, 1991 |
| Peptide hormones | NGF inducer | Wion, et al. FEBS Lett. 189 37-41, 1985 |
| Retinoic acid | NGF inducer | Wion, et al. Biochem. Biophys. Res. Commun. 149 510-514, 1987 |
| Phorbol 12-myristate 13-acetate | NGF inducer | Wion, et al. FEBS Lett. 262 42-44, 1990 |
| Dibutyryl-cyclic AMP | Neuritogenesis inducer | Prasad, et al. Cancer 36 1338 1975 |

Particularly, lactacystin is a microbial metabolite produced by a Streptomyces strain (Omura, et al. J. Antibiotics 44:113-116, 1991).

Methods for treating neurodegenerative diseases by administration of compounds which are able to modulate NGF synthesis or to mimic NGF by correlation with activity in the PC12 pheochromocytoma cell model systems are known in the art (see U.S. Pat. Nos. 5,075,305 and 5,098,902). Additionally, it has been clinically reported that intraperitoneal infusion of NGF supports adrenal medullary autografts in Parkinson's disease (Olsen, et al., Arch. Neurol. 48:373-381, 1991).

It would be highly desirable to identify new compounds which are useful in treating neurodegenerative disease such as Alzheimer's and dementia associated with Parkinson's disease.

SUMMARY OF THE INVENTION

The present invention is based on the discovery of a new microorganism strain which produces a compound which has been found to have antibacterial activity and neuritogenic activity. The compound of the invention has the formula

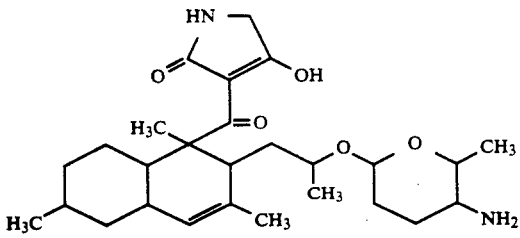

The compound of the invention will be referred to herein as compound "BU-4514N" which term also includes pharmaceutically acceptable salts of the compound. The present invention is also directed to a pharmaceutical composition comprising compound BU-4514N together with a pharmaceutically acceptable carrier.

Compound BU-4514N has been found to be produced by a microorganism identified as belonging to the genus Microtetraspora and designated as species T689-92. Thus, the present invention is also directed to a biologically pure culture of Microtetraspora species T689-92. It is also contemplated that mutants and variants of Microtetraspora species T689-92 are also within the scope of the present invention, whether created by conventional physical or chemical means or by recombinant genetic engineering techniques. The present invention also includes a process for producing a neuritogenic or antibacterial compound comprising cultivating under aerobic conditions Microtetraspora species T689-92 or a mutant or variant thereof in a suitable culture medium containing a carbon source and a nitrogen source at a pH and temperature and for a time sufficient for production of said compound.

Additionally, the present invention is directed to a method for controlling bacteria which comprises applying to said bacteria or habitat thereof an effective amount of compound BU-4514N.

Furthermore, the present invention is directed to a method for enhancing the effect of nerve growth factor in a patient in need thereof which comprises administering to said patient an effective amount of compound BU-4514N.

Finally, the present invention is directed to a method for treating a neurodegenerative disease in a patient in need thereof which comprises administering to said patient an effective amount of compound BU-4514N.

DETAILED DESCRIPTION OF THE INVENTION

Figure 1:
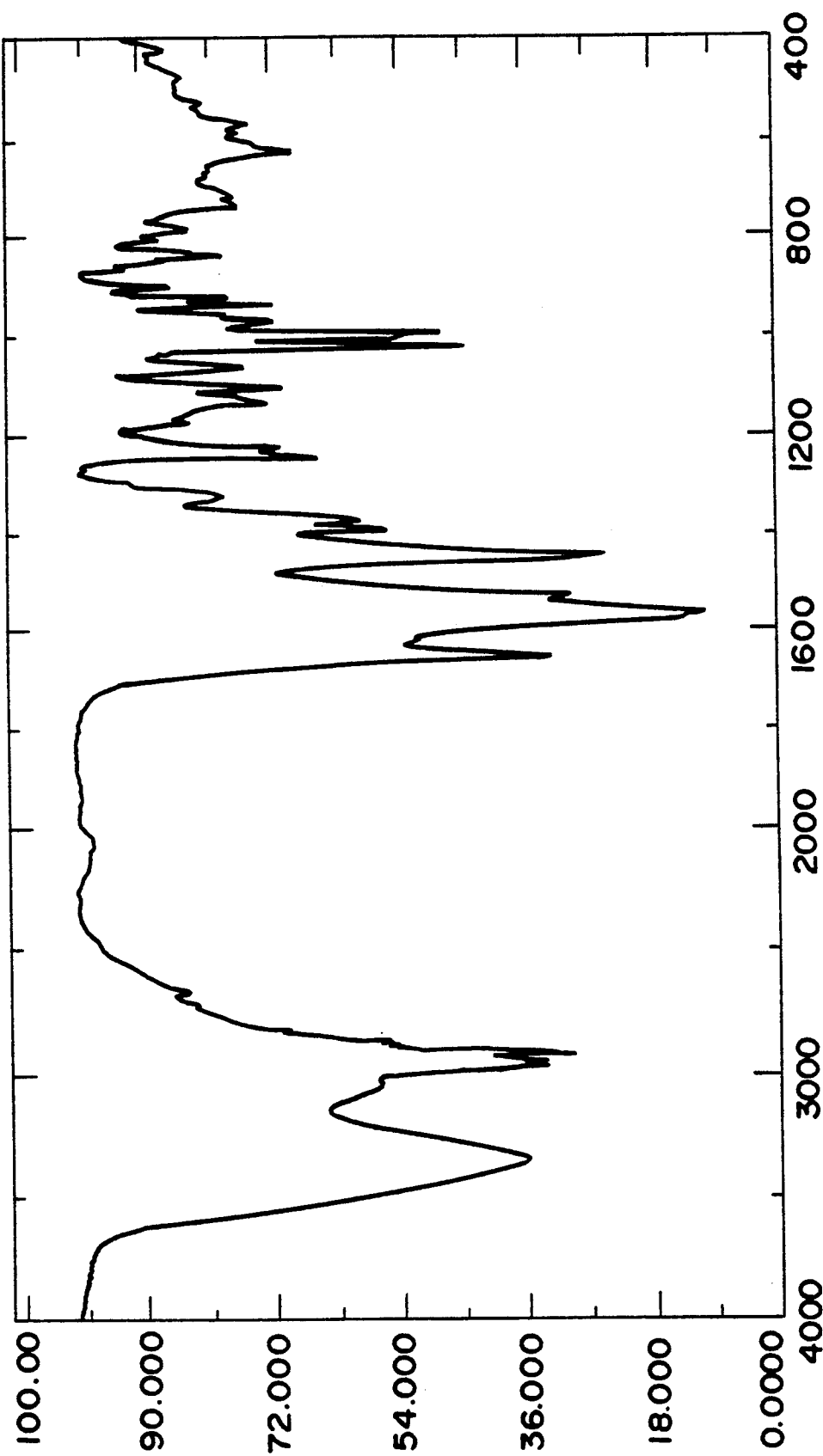
FIG. 1—IR spectrum of BU-4514N.

Microtetraspora species T689-92 was isolated from a soil sample collected in Andhra Pradesh, India. This organism has been deposited on Jan. 31, 1992, with the American Type Culture Collection (ATCC), 12301 Parklawn Drive, Rockville, Md., 20852, U.S.A., under Accession Number ATCC-55291.

It is to be understood that the present invention is not limited to use of the particular Strain T689-92 or to organisms fully answering the description contained herein. It is especially intended to include other BU-4514N producing strains or mutants or variants of said organisms which can be produced from the described organism by known means such as X-ray irradiation, ultraviolet irradiation, treatment with nitrogen mustard, phage exposure, and the like; or through the use of recombinant genetic engineering techniques.

The compound of the present invention is produced by cultivating Microtetraspora species T689-92, or a mutant or a variant thereof, in a conventional aqueous medium. The organism is grown in a nutrient medium containing known nutritional sources for actinomycetes, i.e. assimilable sources of carbon and nitrogen plus optional inorganic salts and other known growth factors. Submerged aerobic conditions are preferably employed for the production of large quantities of antibiotic, although for production of limited amounts, surface cultures and bottles may also be used. The general procedures used for the cultivation of other actinomycetes are applicable to the present invention. The nutrient medium should contain an appropriate assimilable carbon source such as sucrose, xylose, inositol, mannitol, fructose, or rhamnose. As nitrogen sources, ammonium chloride, ammonium sulfate, urea, ammonium nitrate, sodium nitrate, etc. may be used or organic nitrogen sources such as peptone, fish meat extract, yeast extract, corn steep liquor, soybean powder, cotton seed flour, etc. may be used, or any combination thereof. There may also be added if necessary nutrient inorganic salts to provide sources of sodium, potassium, calcium, ammonium, phosphate, sulfate, chloride, bromide, carbonate, zinc, magnesium, manganese, cobalt, iron and the like. Ordinarily, optimum production of BU-4514N is obtained in shake flasks after an appropriate incubation period. Aeration in shake flasks is achieved by agitation, e.g. shaking on a rotary shaker. If fermentation is to be carried out in tank fermentors, it is desirable to produce a vegetative inoculum in a nutrient broth by inoculating the broth culture from a slant culture of a lyophilized culture of the organism. After obtaining an active inoculum in this manner, it is aseptically transferred to the fermentation tank medium. Agitation in the tank fermentor is provided by stirring and aeration may be achieved by injection of air or oxygen into the agitated mixture. Production of BU-4514N may be monitored using chromatographic or spectroscopic techniques, or by a conventional biological assay.

Preferred culture conditions include a pH of about 6 to about 8 and temperature of about 18° C. to about 44° C., and an incubation period of about 3 days to about 8 days. More preferred conditions include a pH of about 7, a temperature of about 31° C. to about 42° C., and an incubation period of about 4 days to about 6 days.

After cultivation and production of the active compound, said compound can be isolated by techniques known in the art and/or taught herein. For example, the fermented whole broth can be extracted by contact with a suitable organic solvent such as n-butanol, n-butyl acetate or 4-methyl-2-pentanone, preferably under agitation. The organic layer can then be separated, e.g. by centrifugation followed by removal of the solvent, e.g. by evaporation to dryness, preferably under vacuum. The resulting residue can then optionally be reconstituted (e.g. in a water ethyl acetate mixture) and re-extracted with a suitable organic solvent. After removal of solvent, the active compound can be further purified/isolated by use of standard techniques such as chromatography, particularly column chromatography, optionally followed by further purification, e.g. by use of reverse phase chromatography. Various modifications to any particular isolation/purification procedure will be apparent to a skilled artisan, but the final sample should show a single peak in a high performance liquid chromatography (HPLC) analysis.

For medicinal use, the pharmaceutically acceptable acid addition salts, those salts in which the anion does not contribute significantly to toxicity or pharmacological activity of their organic cation, are preferred. The acid addition salts are obtained either by reaction of the active compound with an organic or inorganic acid, preferably by contact in solution, or by any of the standard methods detailed in the literature and available to a practitioner skilled in the art. Pharmaceutically acceptable salts of the compound of the invention are illustratively hydrochloric, sulfuric, phosphoric, acetic, benzoic, citric, malonic, salicylic, malic, fumaric, oxalic, succinic, tartaric, lactic, gluconic, ascorbic, maleic, aspartic, benzenesulfonic, methane and ethanesulfonic, hydroxymethane- and hydroxyethanesulfonic. (See, for example, "Pharmaceutical Salts," J. Pharm. Sci. 66(1):1-19 (1977))

Compound BU-4514N has been found to be able to control bacteria, particularly gram positive bacteria. The term "control" refers to antimicrobial activity such as the suppression, inhibition, kill, stasis, or destruction of microorganisms, or any interference with the growth of microorganisms which results in a slower growth rate. The term "effective amount" when used in conjunction with the antimicrobial method of the present invention refers to that amount of compound BU-4514N sufficient to result in control of microorganisms.

Compound BU-4514N can be used in a wide variety of applications in which control of microorganisms is desired. The compound is active against pathogenic and non-pathogenic bacteria which may be resistant to widely used known antibiotics. Because of this activity, BU-4514N can be used as therapeutic agents and administered to a patient in need of antibacterial treatment either orally, parenterally, or topically. As used herein, the term "treatment", whether used in conjunction with the antibacterial method or neuritogenic method of the invention, refers to amelioration, cure, or prevention of the appropriate disease or infection.

Compound BU-4514N or combinations containing the same can also be used as disinfectants, for example, to disinfect objects and instruments. The compound can be used as an antibacterial agent, for example, by contacting bacteria pests or their habitat with effective amounts sufficient to obtain control of many organisms. The compound of this invention can be incorporated into various products susceptible to microbial degradation in order to prevent such degradation of the products by the microorganisms.

Compound BU-4514N is also useful for treating neurodegenerative diseases. In particular, compound BU-4514N is useful in treating senile cognitive decline and Alzheimer's disease. The compound is also useful in treating myasthenia gravis, tardive dyskinesia, and dementia associated with Down's syndrome or Parkinson's disease. This utility of compound BU-4514N in treating these neurodegenerative diseases is demonstrated using culture of PC12 rat pheochromocytoma cells which have been shown to respond to nerve growth factor (NGF) (Tischler and Greene, Nature 258:341-342, 1975). The PC12 rat pheochromocytoma cells respond to NGF by differentiating into sympathetic neuron-like cells. The cells cease dividing, extend processes resembling neurites, and synthesize increased levels of neurotransmitters and neurotransmitter receptors.

Compound BU-4514N can be administered to a patient in need of neurodegenerative disease treatment either orally or parenterally. The amount of compound to be administered for either the antibacterial or neuritogenic method of the invention would depend in part on the age, weight, and general condition of the patient. Typically, a patient would be closely monitored by a physician who could determine if the dosage amount or regimen of compound being administered was effective and well tolerated. Compound BU-4514N would be administered for either antibacterial or neuritogenic method of the invention either alone or admixed with a pharmaceutically acceptable carrier. An effective unit dose of the compound for the neuritogenic method would be from about 5 to about 50 mg/kg of body weight of the patient with a daily dose ranging from about 15 to about 150 mg/kg of body weight of the patient. For the antibacterial method of the invention, a typical effective unit dose of the compound given orally or parenterally would be from about 5 to about 150 mg/kg of body weight of the patient with a daily dose ranging from about 15 to about 450 mg/kg of body weight of the patient.

For preparing pharmaceutical compositions from the compound of this invention, inert, pharmaceutically acceptable carriers can be either solid or liquid. Solid form preparations include powders, tablets, dispersible granules, capsules, cachets, and suppositories.

A solid carrier can be one or more substances which may also act is diluents, flavoring agents, solubilizers, lubricants, suspending agents, binders, or tablet disintegrating agents; it can also be an encapsulating material.

In powders, the carrier is a finely divided solid which is in a mixture with the finely divided active component. In tablets, the active compound is mixed with the carrier having the necessary binding properties in suitable proportions and compacted in the shape and size desired.

For preparing suppositories, a low-melting wax such as a mixture of fatty acid glycerides and cocoa butter is first melted, and the active ingredient is dispersed therein by, for example, stirring. The molten homogeneous mixture is then poured into convenient sized molds and allowed to cool solidly.

Powders and tablets preferably contain between about 5% to about 50% by weight of the active ingredient. Suitable carriers are magnesium carbonate, magnesium stearate, talc, lactose, sugar, pectin, dextrin, starch, tragacanth, methyl cellulose, sodium carboxymethyl cellulose, a low-melting wax, cocoa butter, and the like.

The term "preparation" is intended to include the formulation of the active compound with encapsulating material as a carrier providing a capsule in which the active component (with or without other carriers) is surrounded by a carrier, which is thus in association with it. In a similar manner, cachets are also included.

For topical administration, the compound may be incorporated into lotions, ointments, gels, creams, salves, tinctures, and the like.

Tablets, powders, cachets, and capsules can be used as solid dosage forms suitable for oral administration.

Liquid form preparations include solutions suitable for oral or parenteral administration; suspensions, or emulsions suitable for oral administration. Sterile water solutions of the active component or sterile solutions of the active component in solvents comprising water, ethanol, or propylene glycol may be mentioned as examples of liquid preparations suitable for parenteral administration.

Sterile solutions for injection or infusion may be prepared by dissolving the active component in the desired solvent system, and then passing the resulting solution through a membrane filter to sterilize it or, alternatively, by dissolving the sterile compound in a previously sterilized solvent under sterile conditions.

Aqueous solutions for oral administration can be prepared by dissolving the active compound in water and adding suitable flavorants, coloring agents, stabilizers, and thickening agents as desired. Aqueous suspensions for oral use can be made by dispersing the finely divided active component in water together with a viscous material such as natural or synthetic gums, resins, methyl cellulose, sodium carboxymethyl cellulose, and other suspending agents known to the pharmaceutical formulation art.

Preferably, the pharmaceutical preparation is in unit dosage form. In such form, the preparation is divided into unit doses containing appropriate quantities of the active component. The unit dosage form can be a packaged preparation, the package containing discrete quantities of the preparation, for example, packeted tablets, capsules and powders in vials or ampoules. The unit dosage form can also be capsule, cachet, or tablet itself, or it can be the appropriate number of any of these packaged forms.

The following examples are to illustrate the invention but should not be interpreted as a limitation thereon.

EXAMPLE 1

Taxonomy of Microtetraspora Strain T689-92

Cultural and physiological studies were done by using the media described by Shirling and Gottlieb (Shirling, E. B. and D. Gottlieb: Methods for characterization of Streptomyces species. Inter. J. Syst. Bact. 16:313–340, 1966), Waksman (S. A. Waksman, In The Actinomycetes, Vol. II. Classification, identification and description of genera and species. pp. 328-334. The Williams & Wilkins Co., Baltimore, 1961), Arai (T. Arai, In Culture Media for Actinomycetes. The Society for Acetinomycetes, Japan, 1975), and Gauze (G. F. Gauze, T. P. Preobrazhenskaya, E. S. Kudrina, N. O. Blinov, I. D. Ryabova and M. A. Sveshnikova: Problems in the classification of antagonistic acetinomycetes. State Publishing House for Medical Literature (in Russian), Medzig, Moscow, 1957). Morphological and cultural characteristics were observed after incubation at 37° C. for 2 to 4 weeks according to the procedures recommended by Shirling and Gottlieb. Color names and hue numbers are given according to the Manual of Color Names (Japan Color Enterprise Co., Ltd., 1987). Utilization of carbohydrates and other physiological test were carried out by the methods described by Shirling and Gottlieb and Waksman. Temperature range for growth was determined on yeast starch agar (Arai) using a temperature gradient incubator TN-3 (Toyo Kagaku Sangyo Co., Ltd.).

Biomass for chemotaxonomic analysis were prepared by using lyophilized whole cells grown at 32° C. for 4 days with a rotary shaker in a liquid medium (glucose 1% and yeast extract 1%, pH 7.0). Cell wall analysis was performed by the methods of H. A. Lechevalier and M. P. Lechevalier (A critical evaluation of the genera of aerobic actinomycetes. In The Actinomycetales [H. Prauser, ed.], pp. 393–405. Jena, Gustav Fischer Verlag, 1970) as modified by Staneck and Roberts (J. L. Staneck and G. D. Roberts: Simplified approach to identification of aerobic actinomycetes by thin-layer chromatography. Appl. Microbiol. 28:226–231, 1974). Phospholipid and mycolate composition were determined after Lechevalier (Lechevalier, et al: Chemotaxonomy of aerobic actinomycetes: Phospholipid composition. Biochem. Syst. Ecol. 5:249-260, 1977) and Minnikin (Minnikin, et al: Differentiation of Mycobacterium, Nocardia and related taxa by thin-layer chromatographic analysis of whole-organism methanolysates. J. Gen. Microbiol. 88:200–204, 1975), respectively. Menaquinone was analyzed by the procedure of Collins et al (A note on the separation of natural mixtures of bacterial menaquinones using reverse-phase thin-layer chromatography. J. Appl. Bacteriol. 48:277-282, 1980). Fatty acid was determined by the method of Suzuki et al (Suzuki, et al: Taxonomic significance of cellular fatty acid composition in some coryneform bacteria. Int. J. Syst. Bacteriol. 33:188–200, 1983).

Morphology

Substrate mycelia were well developed, extensively branched and did not fragment into short elements or form spores. Rudimentary and retarded aerial mycelia were only produced on both yeast starch agar and Gauze's I agar, but no sporulating aerial mycelium was observed by scanning electron microscope. Therefore, several attempts to yield sporulating aerial mycelia have been made, without success.

Cultural Characteristics

Strain T689-92 formed good vegetative growth on the media used in this study. Aerial mycelia were only produced on yeast starch agar, Gauze's I agar and maltose-Bennett's agar. They were rudiment without sporulation and were powdery with pale reddish yellow to grayish yellow. The color of vegetative mycelia and reverse side of colony ranged from pale yellow to reddish brown or dull yellow. No diffusible pigment was produced. The macroscopic properties of strain T689-92 on various agar media were summarized in Table 1.

Physiological Characteristics

The physiological characteristics and the utilization of carbon sources were shown in Tables 2 and 3, respectively.

Cell Chemistry

Analysis of hydrolyzed whole cells indicated the presence of meso-diaminopimelic acid with no LL isomer present. Sugar analysis of hydrolyzed whole cells indicated the presence of glucose, galactose, mannose, madurose and ribose. This represents a type III and a type B sugar pattern. Mycolic acids were not detected. By phospholipids analysis, the wall had a type IV containing phosphatydilinositol, diphosphatydilglycerol and unknown glucosamine-containing phospholipid. Analysis of the menaquinone composition revealed 69% MK-9($H_4$), 15% MK-9($H_2$), 10% MK-9($H_6$), 3% MK-9($H_8$) and 3% MK-9($H_0$). Analysis of the fatty acids exhibited high amounts of 14-methylpentadecanoic acid (iso-16:0), 10-methylheptadecanoic acid (10-Meth 17:0) and α-hydroxy-14-methylpentadecanoic acid (iso-16:OH 20H) (Table 4).

A search of published reports concerning the taxonomy of Actinomycetales genera revealed that the above-mentioned characteristics of the strain, especially chemotaxonomic properties are in good agreement with those of the genus Microtetraspora (R. N. Kroppenstedt, et al: Taxonomic revision of the actinomycete genera Actinomadurae and Microtetraspora. System Appl. Microbiol. 13:148-160, 1990), while the morphological properties of strain T689-92 is unable to characterized. Thus, it is concluded that the culture T689-92 represents a species of Microtetraspora.

Strain T689-92 was deposited with the American Type Culture Collection (ATCC), 12301 Parklawn Drive, Rockville, Md. 20852, under the provisions of the Budapest Treaty, under Accession Number ATCC 55291.

FERMENTATION

Seed Culture

A portion (0.3 ml) of vegetative mycelia of the producing strain was inoculated into a 500-ml Erlenmeyer flask containing 100 ml of a seed medium composed of sucrose 3%, fish meal (Hokuyo Suisan Co.) 2%, soybean meal (Nikko Seiyu Co.) 0.5%, peptone (Nihon Seiyaku Co.) 0.2% and $CaCO_3$ 0.6%. The pH of the medium was adjusted to 7.0 before autoclaving. The seed was incubated at 28° C. for 4 days on a rotary shaker operating at 200 rpm.

Flask Fermentation

A 5-ml portion of the seed culture was transferred into a 500-ml Erlenmeyer flask containing 100 ml of a production medium having the same composition as the seed medium. Fermentation was carried out for 6 days under the same conditions as those for the seed culture. The antibiotic activity was determined by the nerve growth factor mimic activity.

TABLE 1

Cultural characteristics of strain T689-92

| Medium | Vegetative mycelium | Reverse Side | Aerial Mycelium | Diffusible Pigment |
|---|---|---|---|---|
| Sucrose nitrate agar (Waksman med. 1) | Pale yellow (128) | Soft reddish yellow (146) | None | None |
| Glycerol nitrate agar | Pale yellow (128) | Soft yellow (147) | None | None |
| Glucose asparagine agar (Waksman med. 2) | Soft reddish yellow (146) | Soft reddish yellow (146) | None | None |
| Yeast extract-malt extract agar (ISP med. 2) | Grayish brown (118)-dark yellowish brown (105) | Yellowish brown (99) | None | None |
| Oatmeal agar (ISP med. 3) | Soft reddish brown (146) | Soft reddish brown (146) | None | None |
| Inorganic salts-starch agar (ISP med. 4) | Gold (162) | Soft reddish yellow (146) | None | None |
| Glycerol asparagine agar (ISP med. 5) | Dull yellow (150) | Dull yellow (150) | None | None |
| Tyrosine agar (ISP med. 7) | Dull yellow (150) | Dull yellow (150) | None | None |
| Nutrient agar (Waksman med. 14) | Gold (161) | Gold (161) | None | None |
| Yeast starch agar | Yellowish brown (98) | Grayish brown (118) | Pale reddish yellow (130), Powdery, Thin | None |
| Gauze's agar | Yellowish brown (99) | Yellowish brown (99) | Grayish yellow (155), Powdery, Thin | None |
| Oatmeal-yeast extract agar | Soft reddish yellow (146) | Soft reddish yellow (146) | None | None |
| Bennett's agar (Waksman med. 30) | Yellowish brown (99) | Yellowish brown (99) | None | None |
| Maltose-Bennett's agar | Soft reddish yellow (146) | Brownish gold (160) | Pale reddish yellow (130) Powdery, Thin | None |

Stocked Culture

Strain T689-92 was propagated on rB agar slant composed of soluble starch (Nichiden Kagaku Co.) 0.5%, glucose 0.5%, meat extract (Mikuni Chemical Industries Co., Ltd.) 0.1%, yeast extract (Oliental Yeast Co.) 0.1%, NZ-case (Humko Sheffield Chemical Co.) 0.2%, NaCl 0.2%, $CaCO_3$ 0.1% and agar (Junsei Chemical Co.) 1.6%, for 7 days at 28° C. A portion of the mature agar slant was inoculated into 100 ml of seed medium in a 500-ml Erlenmeyer flask and incubated for 4 days at 28° C. and 200 rpm on a rotary shaker. The vegetative medium was composed of soluble starch 2%, glucose 0.5%, NZ-case 0.3%, yeast extract 0.2%, fish meal D30X (Banyu Nutrient) 0.5% and $CaCO_3$ 0.3%. The resulting vegetative mycelia were spun down gently (3,000 rpm, 15 min. 4° C.) and resuspended with a half volume of 20% aq. glycerol solution and then stocked in −80° C.

TABLE 2

Physiological Characteristics of Strain T689-92

| Test | Results |
|---|---|
| Starch hydrolysis (On ISP med. No. 4) | Positive |
| Nitrate reduction (Difco, nitrate broth) | Positive |
| Milk (Difco, 10% skimmed milk) | |
| Coagulation | Positive |
| Peptonization | Positive |
| Cellulose decomposition (sucrose nitrate solution with a paper strip as the sole carbon source) | Negative |
| Gelatin liquefaction | |
| On plain gelatin | Negative |
| On glucose peptone gelatin | Negative |
| Melanin formation (On ISP med. No. 7) | Negative |
| Temperature range for growth (°C.) | 18–44 |
| Optimum temperature (°C.) (On Yeast starch agar) | 31–42 |
| pH range for growth | 6–8 |
| Optimum pH (On Trypticase soy broth, BBL) | 7 |

TABLE 3

Utilization of Carbon Sources by Strain T689-92

| Carbon Source | Growth |
|---|---|
| D-Glucose | ++ |
| L-Arabinose | ± |
| D-Xylose | + |
| Inositol | ++ |
| Mannitol | + |
| D-Fructose | + |
| L-Rhamnose | + |
| Sucrose | + |
| Raffinose | − |

−: Negative
±: Doubtful
+: Weak positive
++: Strong positive
(ISP med. No. 9, 37° C. for 21 days)

TABLE 4

Fatty Acid Composition of Strain T689-92
Fatty Acid Composition (%)

| Straight Chain | | | | Branched Chain | | | | | | Unsaturated Chain | | | | | |
|---|---|---|---|---|---|---|---|---|---|---|---|---|---|---|---|
| 14:0 | 15:0 | 16:0 | 17:0 | i-14 | i-15 | i-16 | i-18 | a-17 | 15:1$^9$ | i-16:1 | 16:1$^9$ | i-18:1$^9$ | 10Me16 | 10Me17 |
| 1 | 2 | 2 | 3 | 1 | 3 | 26 | 1 | 5 | 1 | 4 | 2 | 1 | 1 | 21 |
| 10Me18 | 2OH15 | i-2OH16 | 2OH16 | i-2OH17 | OH17:0 |
| 4 | 1 | 10 | 2 | 1 | 2 |

EXAMPLE 2

Compound BU-4514N

Isolation, Chemical Properties and Structure

Isolation

The harvested whole broth (9.0 L) was extracted by stirring with n-butanol (4.5 L). The organic layer was separated by the aid of a Sharples centrifuge (Kokusan No. 4A) and evaporated to dryness under reduced pressure. The residue was dissolved in a mixture of ethyl acetate and water (1:1, 1.5 L). After stirring 15 minutes, aqueous layer was separated and re-extracted with n-butanol (750 ml). The n-butanol extract was evaporated under reduced pressure to give 2.38 g of crude product which was applied on a column of silica gel (Wakogel C-200, 600 ml). The column was developed with $CH_2Cl_2$:EtOH (1:1, 1 L) and $CH_2Cl_2$: EtOH: conc. $NH_4OH$:$H_2O$ (10:10:1:1, 2.2 L), successively. The eluate was collected in 20-ml fractions and each fraction was monitored by TLC ($SiO_2$:$CH_2Cl_2$:EtOH:conc. $NH_4OH$:$H_2O$ (4:7:1:1) and nerve growth factor mimic activity. The active fractions were combined and evaporated to dryness to give 617 mg of light brown powder. This sample was chromatographed on a reversed phase silica gel column (YMC GEL ODS A60; Yamamura Chemica Lab., 700 ml) using aqueous acetonitrile (40%–80%) containing 0.1% of trifluoroacetic acid as an eluant. The eluate was monitored by TLC ($SiO_2$:$CH_2Cl_2$:EtOH:conc. $NH_4OH$:$H_2O$ (4:7:1:1) and the activity. The active fractions were combined and evaporated under reduced pressure to afford 603 mg of white amorphous powder. This sample showed a single peak in an HPLC analysis (column: YMC-Pack (A-301-3) 4.6 mm I.D.×100 mm, Yamamura Chemical Lab., mobil phase:$CH_3CN$:$H_2O$:trifluoroacetic acid (50:50:0.1), flow rate: 1 ml/minutes, detection:UV absorption at 254 nm) and was crystallized from aqueous methanol to give colorless fine needles.

Physico-chemical Properties

Figure 2:
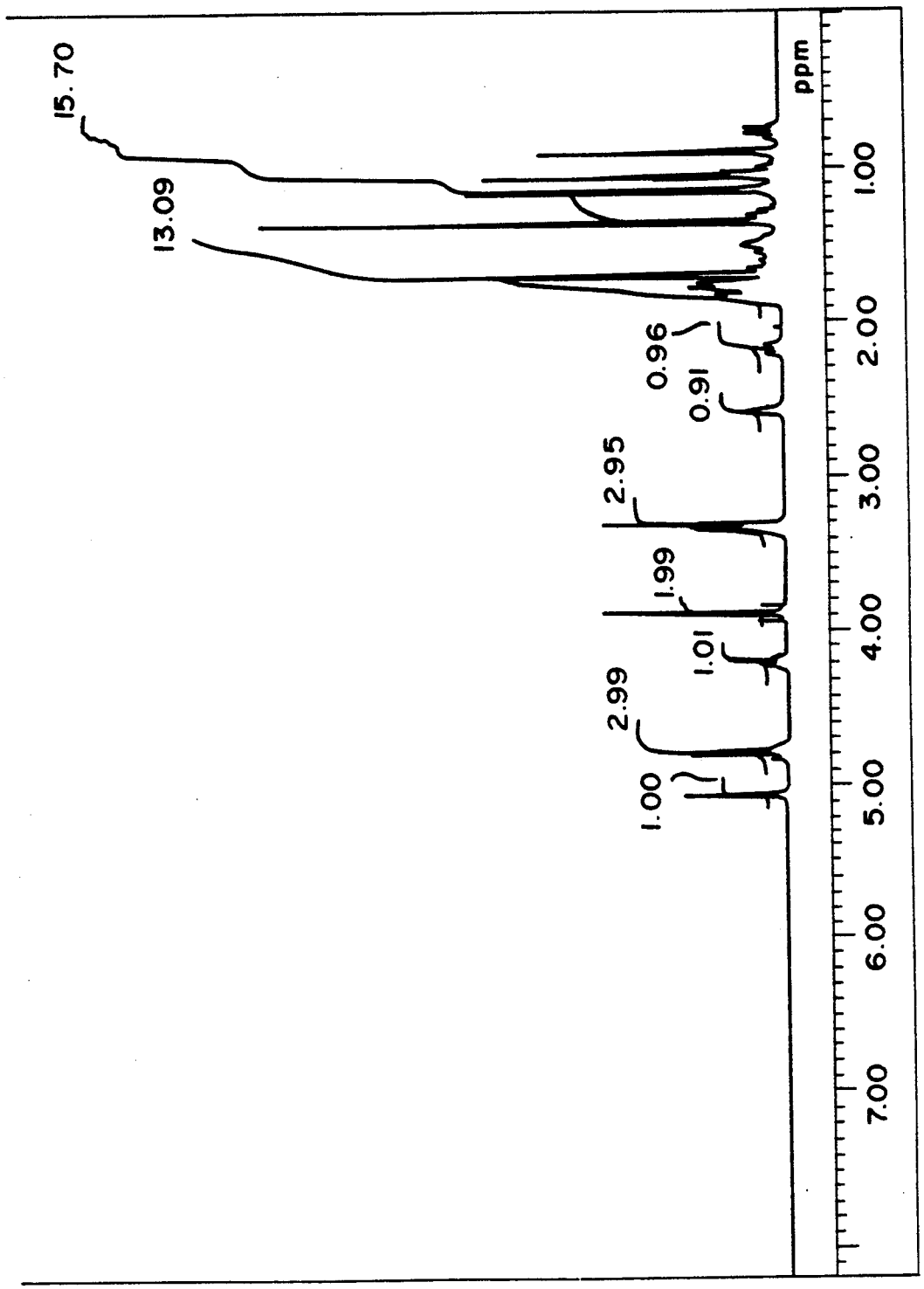
FIG. 2—$^1$H NMR spectrum of BU-4514N.

BU-4514N was obtained as colorless fine needles and its physico-chemical properties are summarized in Table 5. BU-4514N is practically insoluble in water and ordinary organic solvents, such as chloroform, ethyl acetate and benzene. But it is soluble in acidic water, dimethylsulfoxide and methanol. It showed positive responses to iodine, ferric chloride and ninhydrin reagents on TLC plate and negative to Sakaguchi reaction. The UV spectrum of BU-4514N exhibited maxima at 249 nm and 286 nm in methanol. The IR and $^1H$ NMR spectra of BU-4514N are shown in FIG. 1 and FIG. 2, respectively. The $^{13}C$ NMR spectrum of BU-4514N revealed 27 carbon signals (Table 6). The molecular formula of this compound was established to be $C_{27}H_{42}N_2O_5$ by FAB-MS spectrum and microanalysis

Structural Studies

Figure 3:
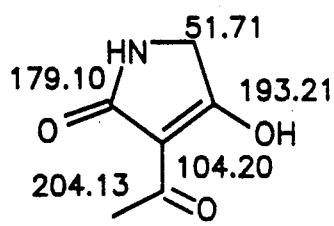
FIG. 3—$^{13}$C NMR data for α-acyltetramic acid moiety of BU-4514N and structure of lydicamycin.
Figure 4:
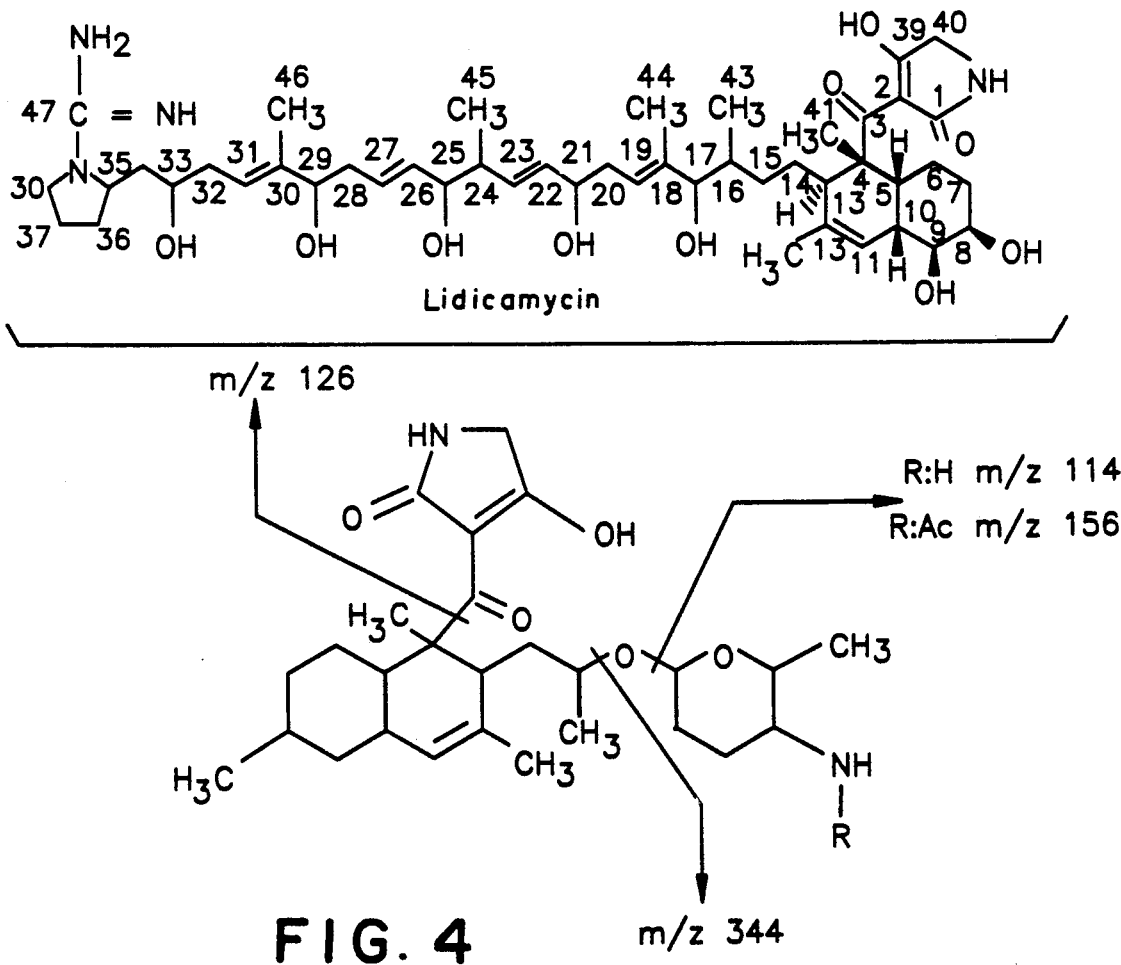
FIG. 4—FAB-MS fragmentation of BU-4514N and its acetate.

The specific UV absorption maxima of BU-4514N under acidic and basic conditions are quite similar to those of lydicamycin (Hayakawa, et al: Lydicamycin, a new antibiotic of a novel skeletal type. II. Physico-chemical properties and structure elucidation. J. Antibiotics 44:288–292, 1991) which showed positive response to ferric chloride reaction. These suggest the presence of α-acyltetramic acid. The $^{13}C$ NMR spectrum demonstrated 27 carbons which are identified as five methyl, seven methylene, nine methyne and six quaternary carbons. The signals at δ204.13, 193.21, 179.10, 104.20 and 51.71 are good agreement with those of α-acyltetramic acid moiety in lydicamycin, (FIG. 3). Acetylation of BU-4514N with acetic anhydride in methanol gave a monoacetate, which showed negative ninhydrin response. Proton NMR spectrum in DMSO-d$_6$ of the acetate gave an NH signal at δ7.78 (1H, d, J=9.0 Hz) and an acetyl signal at δ1.87 (3H, s). These data indicated the presence of >CH-NH$_2$ in the molecule. The FAB-MS spectrum of BU-4514N showed fragment ion peaks at m/z 475 (M+1), 344, 126 and 114, while the acetate gave fragment peaks at m/z 517 (M+1), 344, 156 and 126 (FIG. 4). The analysis of $^1H$-$^1H$, $^1H$-$^{13}C$ and $^1H$-$^{13}C$ long range COSY spectra and previously indicated physico-chemical data reveal the total structure of BU-4514N as shown below:

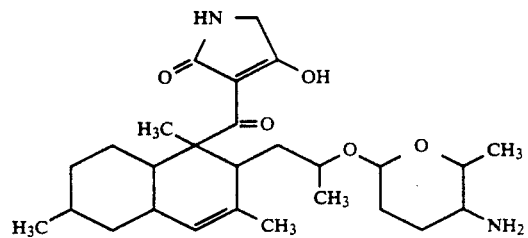

Acetylation of BU-4514N

To a solution of BU-4514N (161 mg) and triethylamine (35 mg) in methanol (20 ml) was added acetic anhydride (95 mg) and the mixture was stirred at room temperature for 5 hours. The reaction mixture was diluted with water (20 ml) and was applied on a column of Diaion HP-20 (Mitsubishi Chemical Industries Ltd., 20 mm I.D.×250 mm), and the column was eluted with 50% aqueous methanol (200 ml), 50% aqueous acetonitrile (200 ml) and 80% aqueous acetonitrile (400 ml), successively. The fractions containing desired compound were pooled, concentrated to dryness to give 149 mg of white amorphous powder. MP 139°–141° C. UV $\lambda_{max}$ (MeOH) nm($\epsilon$) 286(8930), 248(6450), 204(11500).

IR $\nu_{max}$ (KBr)cm$^{-1}$ 3440, 2830, 1660, 1545, 1455, 1380 1115, 1020, 975.

$^1$H NMR (DMSO-d$_6$) δ0.77 (1H, q, J=12.04 Hz), 0.87 (3H, d, J=6.45 Hz), 0.88 (3H, d, J=6.45 Hz), 0.97 (3H, d, J=5.78 Hz), 1.65 (3H, s), 1.87 (3H, s), 3.62 (1H, br), 3.75 (1H, brd, J=9.13 Hz), 3.85 (1H, d, J=19.07 Hz), 3.96 (1H, dq, J=6.45 & 1.88 Hz), 4.58 (1H, br), 5.03 (1H, brs), 7.78 (1H, d, J=9.00 Hz), 9.29 (1H, br).

FAB-MS (m/z) 517(M+1)$^+$, 344, 156, 126.

TABLE 5

Physico-chemical Properties of BU-4514N

| | |
|---|---|
| Nature | colorless fine needles |
| Melting point | 185–186° C. |
| Optical rotation | $[\alpha]^{25}$ −140 ± 1° (c. 0.5, 0.1N HCl) |
| Mass (FAB-MS) m/z | 475 (M + H)$^+$ |
| Molecular formula | C$_{27}$H$_{42}$N$_2$O$_5$ |
| Elemental analysis | |
| Calcd for C$_{27}$H$_{42}$N$_2$O$_5$·$\frac{3}{4}$H$_2$O | C 66.43, H 8.98, N 5.74 |
| Found | C 66.21, H 8.94, N 5.66 |
| UV $\lambda_{max}$ nm($\epsilon$) | |
| MeOH | 286(8530), 251(4360), 204(6300) |
| 0.01N HCl/MeOH | 286(9000), 254sh(4320), 204(6540) |
| 0.01N NaOH/MeOH | 287(8200), 248(9200), 205(8440) |
| IR $\nu_{max}$(KBr) | 3350, 2970, 2930, 1650, 1565, 1530 1445, 1240, 1110, 1020, 995 cm$^{-1}$ |

TABLE 6

$^{13}$C and $^1$H NMR Spectral Data*$^1$ for BU-4514N

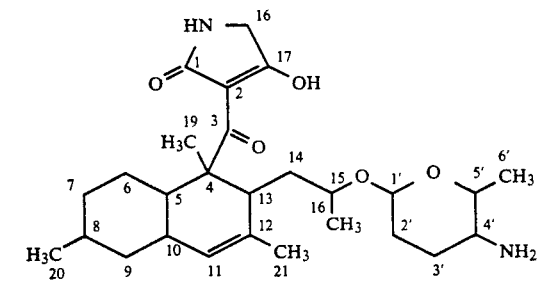

| Carbon No. | $\delta_C$ (multiplicity) | $\delta_H$ (multiplicity) |
|---|---|---|
| 1 | 179.10(s) | |
| 2 | 104.20(s) | |
| 3 | 204.13(s) | |
| 4 | 52.34(s) | |
| 5 | 41.92(d) | 1.55(m) |
| 6 | 29.62(t) | 1.01(m), 1.84(m) |
| 7 | 37.72(t) | 1.06(m), 1.74(m) |
| 8 | 35.34(d) | 1.46(m) |
| 9 | 44.27(t) | 0.76(q, J=12.4Hz), 1.76(m) |
| 10 | 41.36(d) | 1.78(m) |
| 11 | 126.10(d) | 5.07(brs) |
| 12 | 137.56(s) | |
| 13 | 43.64(d) | 2.57(br) |
| 14 | 42.90(t) | 1.32(m), 1.53(m) |
| 15 | 78.71(d) | 3.35(m) |
| 16 | 23.78(q) | 1.04(d, J=5.98Hz) |
| 17 | 193.21(s) | |
| 18 | 51.71(t) | 3.88(d, J=18.81Hz), 3.92(d, J=18.81Hz) |
| 19 | 15.65(q) | 13.4(s) |
| 20 | 24.01(q) | 0.89(d, J=6.84Hz) |
| 21 | 23.70(q) | 1.69(s) |
| 1' | 100.49(d) | 4.79(brs) |
| 2' | 24.93(t) | 1.66(m), 1.82(m) |
| 3' | 23.70(t) | 1.86(m), 2.17(m) |
| 4' | 51.04(d) | 3.32(m) |
| 5' | 65.34(d) | 4.21(dq, J=6.84Hz & 1.28Hz) |
| 6' | 18.14(q) | 1.13(d, J=6.84Hz) |

*$^1$in a mixture of CD$_3$OD/D$_2$O/4NDCl (1:1:0.08)

EXPERIMENTAL

Cells and Cultivation

PC 12R cells derived from PC 12 cells have a sensitivity as high as 1 ng/ml to NGF, and were cultured in Opti-MEM medium (GIBCO) containing 5% heat-inactivated fetal bovine serum (GIBCO) and 50 μg/ml of amikacin (Bristol-Myers Squibb), in a humidified atmosphere of 5% CO$_2$ and 95% air at 37° C. to a cell density of approximately 1×10$^8$ cells per 175 cm$^2$ tissue Culture flask (Lux).

Assay for the Neurite Outgrowth

The PC 12R cell density was adjusted to 1×10$^5$ cells/ml and 180 μl aliquots of the cell suspension were added to assay wells in a 96 well microtiter plate (Suimitomo). For tests, 0.1 ng/ml NGF (Biomedical Technologies Inc. #BT-206) was first added to a well. For the positive controls, 5.0 ng/ml NGF was added to a well. As negative controls, PC 12R cells without NGF were also prepared. Cultures were pre-incubated for 3 hours at 37° C. in a 5% CO$_2$-95% air environment. Then a 20 μl aliquot of a test sample at varied concentrations was added to the test well containing PC 12R cells pre-treated with 0.1 ng/ml NGF. After 24 hours' incubation, the medium was removed and the cells were fixed with 0.3% glutaraldehyde (Tokyo Kasei) in Dulbecco's phosphate buffered saline and stained with Harris hematoxylin solution (Merck).

The stained cells were observed under a phase-contrast microscope connected with a video camera-CRT system. PC 12R cells were magnified 500 times on the CRT monitor. The lengths of spikes of the negative control cells were measured in order to establish the standard length of a spike of the PC 12R cells.

Tentatively positive is a test cell which contains the same or a higher number than the positive control of neurites which are over 10 mm long as composed with the standard length.

Assay for the Antibacterial Activity

The MIC's of BU-4514N against various test microorganisms were determined by the serial 2-fold dilution method after overnight incubation at 32° C. Nutrient agar medium (Difco) was used for Gram-positive and Gram-negative bacteria.

Results

BU-4514N significantly induces the neurite outgrowth in number and length at a concentration range from 12.5 to 6.3 μg/ml, compared to the negative control cells (Table 7).

BU-4514N shows good in vitro antibacterial activity against Gram-positive bacteria (Table 8).

TABLE 7
Neurite Outgrowth Activity of BU-4514N and NGF

| Compound | Concentration | No. of Neurites*/ No. of Cells** | Ratio (%) |
|---|---|---|---|
| 4514N | 12.5 μg/ml | 244/1123 | 21.7 |
| | 6.3 μg/ml | 149/1570 | 9.5 |
| | 3.1 μg/ml | 25/1848 | 1.4 |
| | 1.6 μg/ml | 2/1611 | 0.12 |
| NGF | 0.1 ng/ml | 2/1565 | 0.13 |
| | (Running control) | | |
| | 5 ng/ml | 72/1053 | 6.8 |
| | (Positive control) | | |
| | 0 ng/ml | 0/1298 | 0 |
| | (Negative control) | | |

*Total number of neurites over 10 mm long (observed on the monitor; sum of 5 fields/well and 3 wells/concentration)
**Total number of cells (sum of 5 fields/well and 3 wells/concentration)

TABLE 8
Antibacterial Activity of BU-4514N

| Test Organism | | MIC (μg/ml) |
|---|---|---|
| S. aureus | FDA 209P JC-1 | 1.6 |
| S. aureus | Smith | 3.1 |
| S. aureus | A15036 (MRSA) | 3.1 |
| M. luteus | PCI 1001 | 1.6 |
| B. subtilis | PCI 219 | 0.8 |
| E. coli | Juhl A15119 | >100 |
| E. coli | K12 | >100 |
| E. coli | NIHJ JC-2 | >100 |
| K. pneumoniae | PCI 602 | >100 |
| C. fleundii | GN 7391 | >100 |
| S. typhi | 901 | >100 |
| P. aeruginosa | A9843A | >100 |

Medium: Nutrient Agar, pH 7.0
Inoculum size: $10^5$ cells/ml
Incubations: 32° C., 18 hr The invention has been described in detail with particular reference to preferred embodiments thereof, but it will be understood that variations and modifications can be effected within the spirit and scope of the invention.

We claim:

1. A compound of the formula:

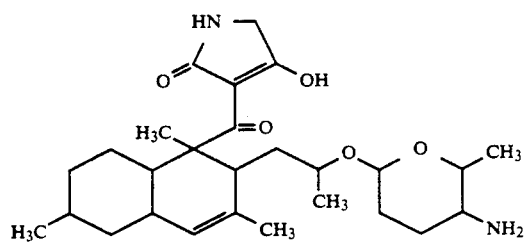

or a pharmaceutically acceptable salt thereof.

2. A pharmaceutical composition comprising a compound of formula

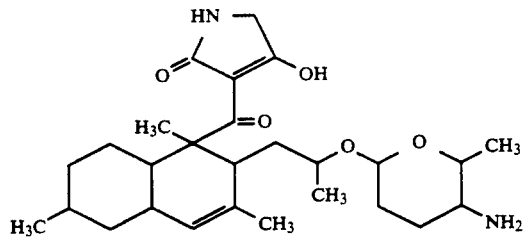

or a pharmaceutically acceptable salt thereof, together with a pharmaceutically acceptable carrier.

3. The composition of claim 2 wherein the amount of said compound comprises about 5 to about 50 weight % of said composition.

4. A method for controlling bacteria which comprises applying to said bacteria or habitat thereof an effective amount of a compound of the formula

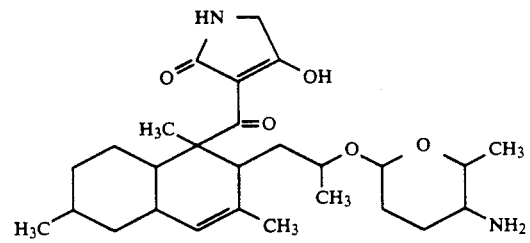

or a pharmaceutically acceptable salt thereof.

5. The method of claim 4 wherein said bacteria are gram positive bacteria.

6. The method of claim 4 wherein a dose of said compound administered is about 5 to about 150 mg/kg of body weight.

7. The method of claim 4 wherein the amount of said compound administered is about 15 to about 450 mg/kg of body weight per day.

8. A method for enhancing the effect of nerve growth factor in a patient in need thereof which comprises administering to said patient an effective amount of a compound of the formula

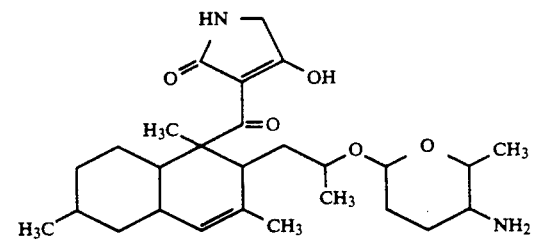

or a pharmaceutically acceptable salt thereof.

9. A method for treating a neurodegenerative disease in a patient in need thereof which comprises administering to said patient an effective amount of a compound the formula

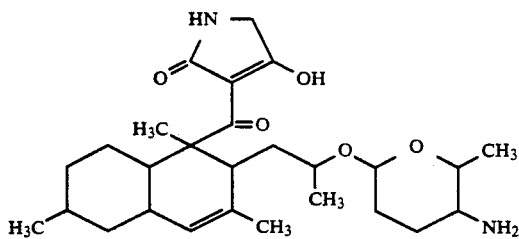

or a pharmaceutically acceptable salt thereof.

10. The method of claim 9 wherein said neurodegenerative disease is senile cognitive decline, Alzheimer's disease, myasthenia gravis, tardive dyskinesia, dementia associated with Down's syndrome, or dementia associated with Parkinson's disease.

11. The method of claim 9 wherein said neurodegenerative disease is Alzheimer's disease.

12. The method of claim 9 when said neurodegenerative disease is senile cognitive decline.

13. The method of claim 9 when said neurodegenerative disease is dementia associated with Parkinson's disease.

14. The method of claim 9 when a dose of said compound administered is about 5 to about 50 mg/kg of body weight.

15. The method of claim 9 wherein the amount of said compound administered is about 15 to about 150 mg/kg. of body weight per day.

* * * * *